United States Patent [19]

Fechtner

[11] Patent Number: 5,075,082

[45] Date of Patent: * Dec. 24, 1991

[54] REAGENT CARTRIDGE

[75] Inventor: Harold F. Fechtner, Claremont, Calif.

[73] Assignee: Beckman Instruments, Inc., Fullerton, Calif.

[*] Notice: The portion of the term of this patent subsequent to Nov. 13, 2007 has been disclaimed.

[21] Appl. No.: 565,796

[22] Filed: Aug. 10, 1990

Related U.S. Application Data

[63] Continuation of Ser. No. 396,769, Aug. 18, 1989, Pat. No. 4,970,053, which is a continuation of Ser. No. 884,465, Jul. 11, 1986, abandoned.

[51] Int. Cl.⁵ .................... B01L 3/00; G01N 35/00; G01N 35/02
[52] U.S. Cl. ................... 422/102; 206/569; 356/246; 422/58; 422/61; 422/64; 422/72; 422/104; 436/45
[58] Field of Search ............. 422/58, 61, 63, 64, 422/67, 72, 102, 104; 436/45, 43; 356/246; 206/569

[56] References Cited

U.S. PATENT DOCUMENTS

| | | | |
|---|---|---|---|
| D. 149,313 | 4/1948 | Shapiro . | |
| D. 159,762 | 8/1950 | Touhey | D44/6 |
| D. 237,655 | 11/1975 | Engelsher | D38/12 A |
| D. 250,834 | 6/1976 | Ruppert | D24/1.1 |
| D. 261,552 | 10/1981 | Boroda | D24/41 |
| D. 276,264 | 11/1984 | Boris | D24/8 |
| D. 276,265 | 11/1984 | Boris | D24/8 |
| D. 276,266 | 11/1984 | Boris | D24/8 |
| D. 276,267 | 11/1984 | Boris | D24/8 |
| D. 276,268 | 11/1984 | Boris | D24/8 |
| D. 276,269 | 11/1984 | Boris | D24/8 |
| D. 276,270 | 11/1984 | Boris | D24/8 |
| D. 276,271 | 11/1984 | Boris | D24/8 |
| 3,295,710 | 1/1967 | Marchant | 220/23.8 |
| 3,554,705 | 1/1971 | Johnston et al. | 23/253 |
| 3,582,285 | 6/1971 | Hamilton | 23/259 |
| 3,713,985 | 1/1973 | Astle | 195/103.5 R |
| 3,788,815 | 1/1974 | Rohrbagh | 23/253 |
| 3,883,305 | 5/1975 | Hoskins et al. | 23/253 |
| 3,905,772 | 9/1975 | Hartnett | 422/72 |
| 3,907,505 | 9/1975 | Beall | 422/102 |
| 3,964,831 | 6/1976 | Frank | 356/182 |
| 3,964,867 | 6/1976 | Berry | 23/253 |

(List continued on next page.)

FOREIGN PATENT DOCUMENTS

| | | | |
|---|---|---|---|
| 136125 | 4/1985 | European Pat. Off. | 422/102 |
| 0216026 | 4/1987 | European Pat. Off. . | |
| 0223002 | 5/1987 | European Pat. Off. . | |
| 0217000 | 8/1987 | European Pat. Off. . | |
| 8300296 | 2/1983 | World Int. Prop. O. | 422/104 |

Primary Examiner—David L. Lacey
Assistant Examiner—Kimberly A. Trautman
Attorney, Agent, or Firm—William H. May; Gary T. Hampson; Charles Berman

[57] ABSTRACT

A reagent cartridge for use in an automated clinical analyzer, the reagent cartridge including a plurality of storage compartments each including wall members. The reagent cartridge includes connecting members formed integrally with the storage compartments for holding the storage compartments in a fixed relationship with respect to each other and separating the wall members from each other to thus prevent reagent migration between adjacent reagent compartments. Each of the storage compartments includes an access opening and a neck formed about the opening, the neck including a collar that is spaced a predetermined distance from a bottom wall of the associated storage compartment, the predetermined distance adapted to accommodate an automatically controlled reagent transfer probe. The reagent cartridge is adapted to be inserted into slots formed in a reagent cartridge storage apparatus on the automated analyzer, the reagent cartridge and slots together forming a positioning and detent mechanism which removably secures the cartridge in the slot for sure and definite positioning of the cartridge during automatic operation of the analyzer.

27 Claims, 3 Drawing Sheets

U.S. PATENT DOCUMENTS

| | | | |
|---|---|---|---|
| 3,994,594 | 11/1976 | Sandrock | 356/246 |
| 4,043,678 | 8/1977 | Farrell et al. | 356/246 |
| 4,083,638 | 4/1978 | Sandrock | 356/246 |
| 4,178,152 | 12/1979 | Nunogaki | 422/72 |
| 4,200,613 | 4/1980 | Alfrey et al. | 422/71 |
| 4,234,540 | 11/1980 | Ginsberg et al. | 422/64 |
| 4,251,159 | 2/1981 | White | 366/246 |
| 4,274,885 | 6/1981 | Swartout | 422/72 |
| 4,287,155 | 9/1981 | Tersteeg | 422/104 |
| 4,344,768 | 8/1982 | Parker | 422/72 |
| 4,346,056 | 8/1982 | Sakurada | 422/64 |
| 4,360,360 | 11/1982 | Chiknas | 23/230 R |
| 4,371,498 | 2/1983 | Scordato et al. | 422/102 |
| 4,391,780 | 7/1983 | Boris | 422/102 |
| 4,483,925 | 11/1984 | Noack | 422/104 |
| 4,515,753 | 5/1985 | Smith et al. | 422/102 |
| 4,526,756 | 7/1985 | Wong | 422/104 |
| 4,538,727 | 9/1985 | Lalonis | 215/6 |
| 4,595,562 | 6/1986 | Liston et al. | 422/65 |
| 4,640,895 | 2/1987 | Davis | 215/6 |
| 4,647,432 | 3/1987 | Wakatake | 422/64 |

REAGENT CARTRIDGE

This application is a continuation of Ser. No. 07/396,769 filed Aug. 18, 1989, now U.S. Pat. No. 4,970,053, which is a continuation of Ser. No. 06/884,465 filed July 11, 1986, now abandoned.

FIELD OF THE INVENTION

The present invention relates generally to the field of automated clinical chemistry analyzers and more particularly to the storage and transportation of reagents within such analyzers.

BACKGROUND OF THE INVENTION

A number of special purpose analyzers are available for the measurement of various analytes in human body fluid samples. In the past, such analyzers were often adapted to test for a single analyte in a patient sample and may have required extensive operator actions to perform an analysis. For example, the operator might be required to perform manual pipetting of patient sample and reagents into a test chamber or cuvette, manual timing of the reaction, and the manual reading of an arbitrary value from the analyzer that is then compared to previously generated calibration values to obtain a final result. As is readily apparent, largely manually operated analyzers are not suitable for either a large number of patient sample analyses or to performing an analysis in a limited amount of time.

In order to meet the increasing demand for the routine testing of a growing number of analytes as well as for the reduction in overall testing costs and the skill required of the technician/operator, several analyzers are currently available which are partially or fully automated. A typical automated analyzer can analyze a single fluid sample for a plurality of analytes with little or no intervention on the part of an operator.

The number of different analytes or chemistries that an automated clinical analyzer can analyze is often termed the "menu" of chemistries available on the analyzer. An automated analyzer may be designed, for example, to analyze a limited menu of basic chemistries that represent the bulk of the work load in a clinical chemistry laboratory, such as glucose, creatinine, sodium, potassium and the like. On the other hand, other analyzers may offer a much larger menu, sometimes ranging up to 50 or 60 different chemistries. Many of such chemistries may represent relatively low volume chemistries, that is, ones that are required on an infrequent basis as compared to the basic chemistries mentioned above.

Each chemistry run on an analyzer generally requires its own unique reagent or combination of reagents. Although it would be desirable to maintain all of the reagents on the analyzer for each of the chemistries on the menu, most large menu analyzers do not have the storage capacity to do so. Instead, reagents for a subset of the menu are stored on the analyzer at one time. When an analysis is to be run that requires reagents that are not presently stored on board the analyzer, the reagents must be placed onto the analyzer before the analysis is run. If the reagent storage area on analyzer is already full, then reagents for a chemistry not in use are removed and the reagents for the new chemistry are installed in their place. With such an approach, it is desirable that the analyzer maintain as many reagents on board as possible and, further, that reagents be easily removed and replaced so that analyzer down time and operator time can both be minimized.

It is known in the art to use reagent cartridges on automated clinical analyzers to increase the ease with which reagents are handled and decrease the time required to reconfigure the chemistries on board the analyzer. Such cartridges may contain all of the various reagents required for a particular chemistry and may be configured to fit onto a reagent storage rack or wheel within the analyzer.

An example of this type of cartridge is used on the Spectrum TM analyzer manufactured by the Diagnostic Division of Abbott Laboratories in Irving, Texas. The Spectrum analyzer employs a molded plastic reagent cartridge generally in the form of a truncated wedge and containing several chambers for the various reagents required for a chemistry. The reagent cartridge fits into an annular well within a reagent storage wheel on the analyzer and each cartridge is accessed by one or more automatic probes that dip into the cartridge chambers.

The reagent cartridge used on the Spectrum analyzer, however, has several disadvantages which are characteristic of reagent cartridges for automated analyzers. The Spectrum analyzer reagent cartridge has integrally formed common walls between the adjacent reagent chambers. It is believed by Applicant herein that reagents stored in adjacent chambers tend to become contaminated due to migration of the reagents through the common chamber walls. Reagent migration is a problem that has been heretofore unrecognized in the art. It is important because contaminated reagents can give spurious test results which may be life threatening. Reagent migration can also decrease the storage life of the reagents, thus increasing analyzer operating costs. The increased operating costs are particularly apparent where the reagents stored in a cartridge are used infrequently and must be stored for a relatively long period of time until consumed.

From an operator's standpoint, the Spectrum analyzer reagent cartridge is difficult to remove from the instrument. Although the cartridge must be lifted upwardly from the storage wheel, the cartridge provides no convenient means by which it may be grasped from above.

Further, the cartridge and the wheel which receives the cartridge provide no sure indication that the cartridge is properly seated in the wheel. Thus, a misaligned cartridge or debris in the storage wheel can cause improper indexing between the cartridge and the wheel. Since the cartridges are each accessed by automatic probes inserted a predetermined distance into the cartridges, inadequate or improper indexing may result in a collision between the probe tip and the bottom of the cartridge. Although such collisions can be avoided by decreasing the insertion depth of the probe into the cartridge, the resulting distance between the inserted probe tip and the bottom of the cartridge causes unused reagent to be left in the cartridge, further decreasing the cost effectiveness of the automated analyzer. Also, a misaligned cartridge may incorrectly access openings with respect to the probe, causing the probe to impact the cartridge and damaging both the probe and cartridge.

Also, the Spectrum analyzer cartridge have been assembled using what is believed to have been ultrasonic welding which may not form a sure, uniform seam. The result is a cartridge which is costly to manufacture and which has a tendency to leak.

SUMMARY OF THE INVENTION

A reagent cartridge in accordance with the present invention overcomes the limitations and disadvantages described above. Such a cartridge includes a plurality of storage compartments each including wall members and further including connecting members holding the storage compartments in a fixed relationship and separating the wall members from each other. By doing so, the wall members of each storage compartment are distinct and separated from the wall members for the other storage compartments in the cartridge, thus eliminating the reagent migration problem discussed above. The connecting members may take the form of a members at the top and bottom of the cartridge.

Each of the storage compartments includes an access opening comprising a neck and a collar formed on the neck. The collar is spaced from each storage compartment bottom wall by a predetermined distance which is adapted to accommodate the insertion depth of a reagent transfer probe. Thus, the reagent cartridge provides a sure and repeatable indexing mechanism which prevents collisions between the probe tip and the cartridge yet allows efficient utilization of reagent stored within the cartridge.

The collars are adapted to be received by parallel rails included in a reagent storage area of a clinical instrument upon which the cartridge is used. The parallel rails include depressions and the reagent cartridge includes a raised body having teeth adapted to be received in the depressions. The teeth and depressions together form a detent mechanism which positively indexes and retains the cartridge on the parallel rails yet allows the cartridge to be easily inserted into and removed from the reagent storage area. Where the reagent storage area is in the form of a rotatable wheel or carousel about which reagent cartridges are disposed, the detent mechanism is particularly useful to retain a cartridge positively on the parallel rails as the wheel or carousel is rotated. The bottom of the cartridge may also include internal depressions aligned with the access openings to provide further insertion clearance for the probe tip when the probe is inserted into the cartridge.

In the embodiment disclosed herein, the reagent cartridge is formed in two parts, a body and a closing member. The body and closing member are pressed against a plate heated to an elevated temperature which renders plastic the portions of the body and closing member in contact with the plate. The plate is removed and the body and closing member are pressed together to form a uniform weld therebetween. This technique overcomes the difficulties and drawbacks associated with ultrasonic welding of reagent cartridges as is described above.

DETAILED DESCRIPTION

Figure 1:
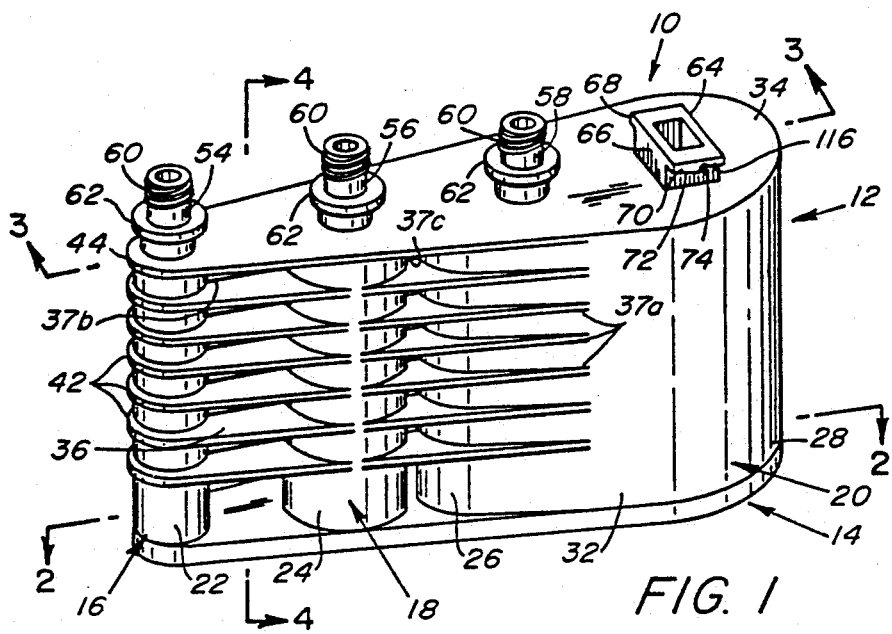
FIG. 1 is a perspective view of a reagent cartridge in accordance with the present invention.
Figure 2:
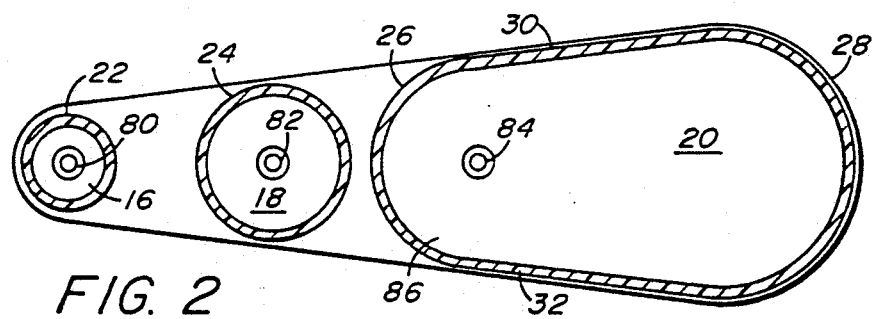
FIG. 2 is a cross-sectional view of the reagent cartridge of FIG. 1 taken along plane 2—2 thereof.

With reference to FIG. 1, a reagent cartridge 10 in accordance with the present invention comprises an upper integrally molded body 12 and a molded bottom member 14. The body 12 and bottom member 14 are welded together as is described hereinbelow to form the completed reagent cartridge 10. The body 12 is formed to define three reagent storage compartments 16, 18 and 20, each adapted to receive and hold reagents for use in a clinical assay. In the embodiment disclosed herein, the volumes of the compartments 16, 18 and 20 are about 5 ml, 25 ml and 125 ml, respectively. Each of the storage compartments 16 and 18 are defined with generally cylindrical side walls 22 and 24, respectively as seen in FIG. 2. The third storage compartment 20 includes side walls generally defined by semicircular end portions 26 and 28 connected by straight wall members 30 and 32.

The body 12 includes a top 34 (FIGS. 1 and 3) which forms the top wall of each of the storage compartments 16, 18 and 20. The top 34 connects and spaces the storage compartments 16, 18 and 20 such that the side walls for the storage compartments 16, 18 and 20 are separated and none of the storage compartments 16, 18 or 20 share a common side wall.

A plurality of webs 36 (FIG. 1, 3 and 4) join the storage compartments 16, 18 and 20 and provide rigidity to the body 12. In the embodiment disclosed herein, the webs 36 comprise six horizontal web members 37a and two vertical web members 37b and 37c between the compartments 16, 18 and 18, 20, respectively. Each of the two vertical web members 37b and 37c terminate near the bottom member 14, defining rectangular openings 38 and 40 therethrough. Outer edges 42 of the horizontal web members 37a are of the same general peripheral outline as an outer edge 44 of the top 34 beginning in the vicinity of the end portion 26 and extending about the storage compartment 16. It will be recognized that the webs 36 may be replaced by other suitable structural means such as solid external walls, ribs, or other structural members arranged in various geometric configurations, all of which are useful for connecting the outer peripheries of the compartments 16, 18 and 20 while still maintaining suitable distance and thus isolation between the reagents stored in each of the compartments 16, 18 and 20. Also, the number of the horizontal webs may be varied from the six disclosed herein, or may be eliminated altogether, relying only on the top 34 and the bottom member 14 to hold the compartments 16, 18, and 20 in place without affecting the physical integrity of the cartridge 10.

Figure 3:
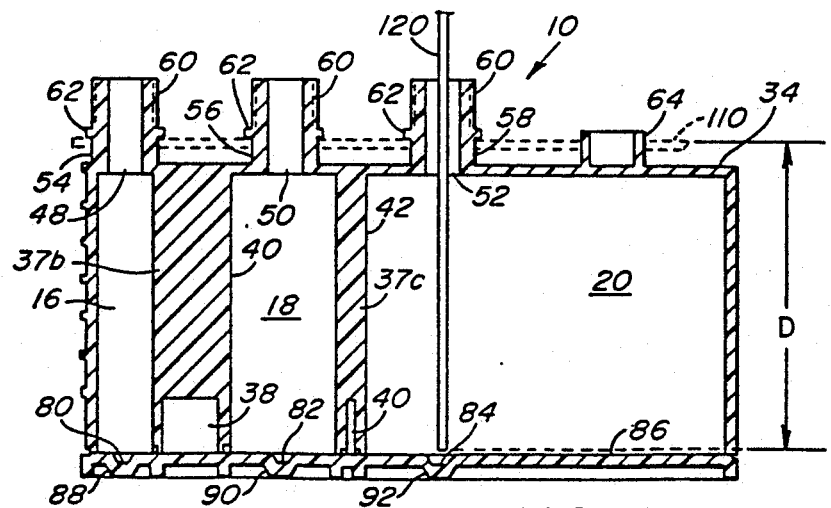
FIG. 3 is a cross-sectional view of the reagent cartridge of FIG. 1 taken along plane 3—3 thereof.
Figure 4:
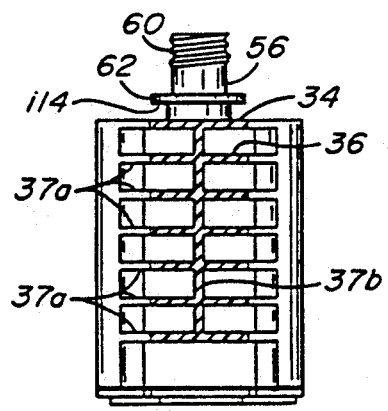
FIG. 4 is a cross-sectional view of the reagent cartridge of FIG. 1 taken across plane 4—4 thereof.

With reference to FIGS. 1 and 3, the body 12 includes openings 48, 50 and 52 formed through the top 34 for access to the storage compartments 16, 18 and 20, respectively. Cylindrical necks 54, 56 and 58 surround the respective openings 48, 50 and 52, the upper portion of the necks 54, 56 and 58 including threads 60 for receiving caps (not shown) for closing the storage compartments 16, 18 and 20. Each of the necks 54, 56 and 58 also includes annular collars 62. The collars 62 are spaced a predetermined distance from the bottom member 14 when the cartridge 10 is assembled as shown in FIG. 1. The collars 62 together define a plane that is parallel to the top 34 and that lies between the top 34 and the threads 60 on each of the necks 54, 56 and 58.

A detent member 64 (FIGS. 1 and 3) is formed on the top 34. The detent member 64 comprises vertical walls 66 projecting upwardly from the top 34 together defining a rectangular body aligned with the necks 54, 56 and 58. The detent member 64 includes flanges 68 and 70 which project outwardly from the walls 66 generally toward the wall members 30 and 32 and in the same plane as the annular collars 62. Each of the flanges 68 and 70 includes a portion 72 which slopes downwardly away from the neck 58 and from the plane defined by the annular collars 62 toward the top 34. Each portion 72 terminates in a tooth 74 which returns to the plane defined by the annular collars 62.

Figure 5A:
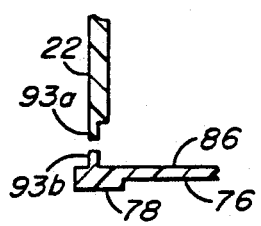
FIG. 5A is a cross-section detail view of typical mating areas between the body and bottom member of the reagent cartridge of FIG. 1.
Figure 5:
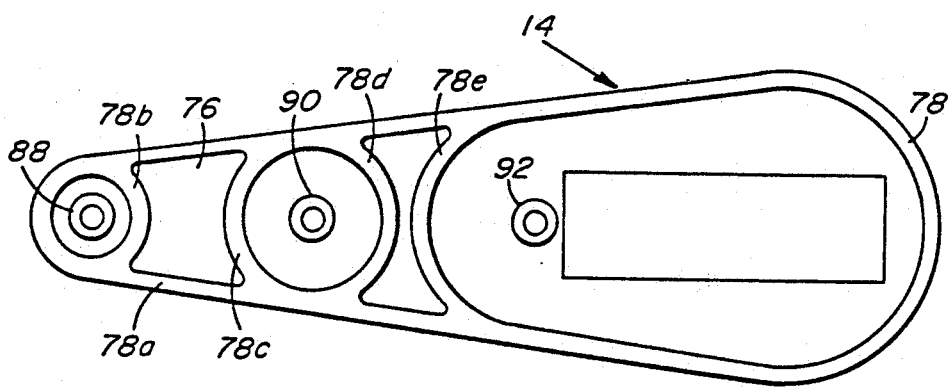
FIG. 5 is a bottom view of the reagent cartridge of FIG. 1.

Turning now to FIGS. 2 and 5, a lower surface 76 of the bottom member 14 includes a raised boss 78. The raised boss 78 includes a peripheral portion 78a extending about the periphery of the bottom member 14 and arcuate portions 78b–78e all of which are opposite the sidewalls 22–32 when the body 12 and bottom member 14 are assembled. Depressions 80, 82 and 84 (FIGS. 2 and 3) are formed into an upper surface 86 of the bottom member 14, producing corresponding protrusions 88, 90 and 92, respectively, on the lower surface 76. When the body 12 and the bottom member 14 are assembled as described below, the depressions 80, 82 and 84 are coaxially aligned with the openings 48, 50 and 52 and the corresponding necks 54, 56 and 58.

The bottom edge of each of the sidewalls 22–32 includes a protruding ridge 93a as illustrated with respect to the sidewall 22 in FIG. 5A. The upper surface 86 of the bottom member 14 includes corresponding protruding ridges 93b adapted to align with the ridges 93a when the body 12 and bottom member 14 are assembled as described hereinbelow.

Figure 6:
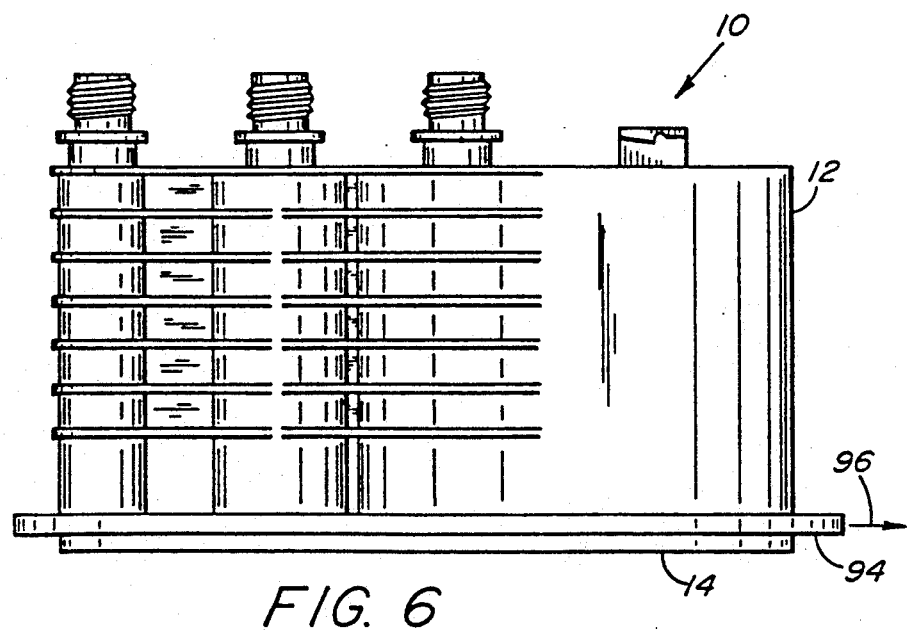
FIG. 6 is a side view of the body and bottom member of the reagent cartridge and a plate used to weld such elements together.

To assemble the reagent cartridge 10, the body 12 and bottom member 14 are pressed against a plate 94 (FIG. 6) which is heated to a temperature sufficient to render plastic and thus fusible the ridges 93a of the body 12 and the corresponding mating ridges 93b on the upper surface 86. The plate 94 is then removed as indicated by the arrow 96 in FIG. 6 and the body 12 and bottom member 14 are urged together, welding the body 12 to the bottom member 14. In the embodiment disclosed herein, the body 12 and bottom member 14 are formed by means of injection molding from high density polyethylene material. To prevent the polyethylene material from sticking to the heated plate 94, the plate 94 is coated with a non-stick material marketed under the trademark Teflon, allowing clean removal of the plate 94 and uniformly high quality and reliable welds between the body 12 and the bottom member 14.

Figure 7:
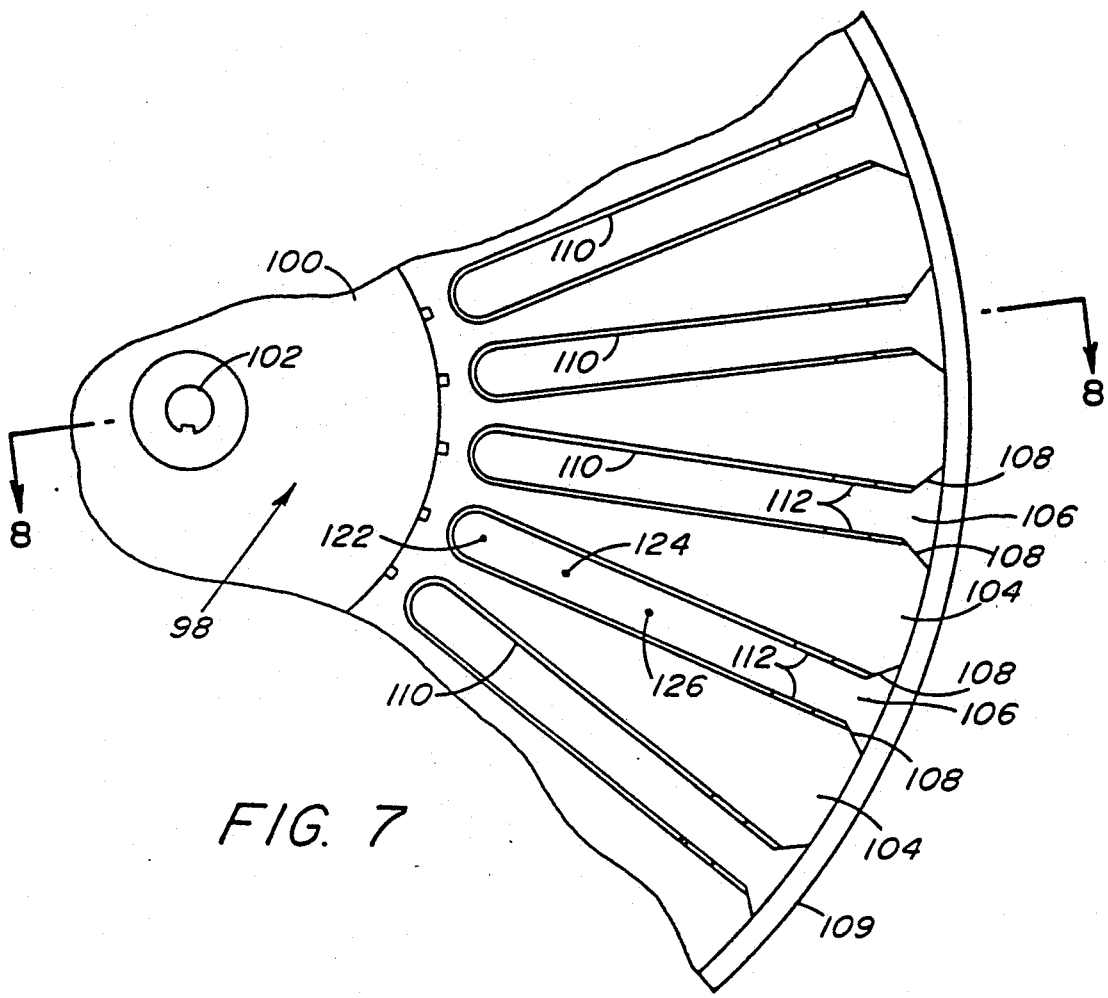
FIG. 7 is a top view of a portion of a reagent cartridge carousel adapted to receive the reagent cartridge of FIG. 1.
Figure 8:
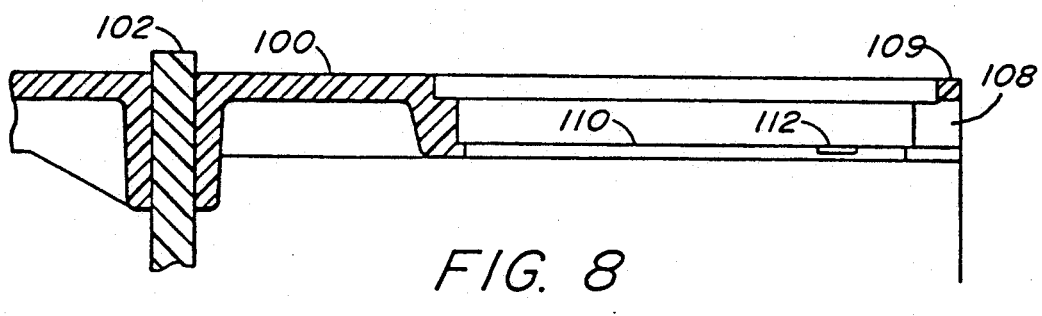
FIG. 8 is a cross-sectional view of the carousel of FIG. 7 taken along line 8—8 thereof.

With reference now to FIGS. 7 and 8, the reagent cartridge 10 may be inserted onto and carried by a reagent cartridge carousel 98. The carousel 98 is rotatably mounted to an automated clinical instrument (not shown) and is preferably automatically rotated to position one of a plurality of reagent cartridges 10 carried by the carousel 98 for the removal of reagents using a probe as is described below. The carousel 98 includes a central hub 100 which receives a shaft 102 rotatably supported by the automated analyzer. For example, the shaft 102 may be rotated by means of a stepper motor under the control of a microprocessor-based computer system which controls the operation of the analyzer. The hub 100 supports a plurality of radial fingers 104 which in turn define a plurality of slots 106 disposed radially about the hub 100. The side walls of each of the slots 106 expand outwardly near the periphery of the carousel 98 to define tapered openings 108. A peripheral reinforcing member 109 is formed about the edge of the carousel 98 to add rigidity to the carousel 98. The reinforcing member 109 is above the tapered openings 108 as seen in FIG. 8 to provide a clear path for insertion and removal of the reagent cartridge 10 as is described below. Each of the slots 106 includes an internal shoulder 110. Depressions 112 are formed into the shoulder 110 proximate the periphery of the carousel 98.

As will now be described, a plurality of cartridges 10 may be inserted onto and carried by the carousel 98. In the embodiment disclosed herein, the carousel 98 may be disposed in a refrigerated environment to maintain the reagents stored in the cartridges 10 at a temperature of about 8° to 10° C. More particularly, the slots 106 are adapted to receive the necks 54, 56 and 58 and the detent member 64 on the top 34 of the reagent cartridge 10. The storage compartment 16 at the narrow end of the cartridge 10 is inserted first into one of the slots 106 and surface 114 of the annular collars 62 and surface 116 of flanges 68 and 70 rest upon and are supported by the shoulder 110 in the slot 106. With the reagent cartridge 10 fully inserted into the slot 106, the portions 72 of the detent member 64 come to rest in the notches 112 and the teeth 74 rest against the edge of the notches 112 nearest the periphery of the carousel 98. In this fashion, the cartridge 10 is retained on the carousel 98 and the carousel 98 may be rotated by the shaft 102 without displacing the cartridge 10 by centrifugal force. Furthermore, the combination of the shoulder 110 and the collars 62 along with the notches 112 and teeth 74 serve to position the cartridge accurately on the carousel 98 for positive and repeatable access by a reagent removal probe.

As seen with reference to FIGS. 3 and 7, such a reagent removal probe 120 is carried by an automated crane well known in the art (not shown) which positions the probe 120 over predetermined probe insertion locations 122, 124 and 126. The insertion locations 122, 124, and 126 are generally coaxially aligned with the necks 54, 56 and 58 when a cartridge 10 is installed on the carousel 98 as just described and the carousel 98 is rotated to a reagent removal position for the cartridge 10. The automated crane also lowers the probe 120 at any one of the locations 122, 124 and 126 to a predetermined insertion depth D with respect to the shoulder 110 shown in phantom in FIG. 3. Thus, the shoulder 110 and the collars 62 along with the notches 112 and teeth 74 repeatably and precisely align the cartridges 10 with respect to the probe insertion locations 122, 124 and 126 and the insertion depth D. Accordingly, probe insertion will not result in collisions between the probe 120 and the top of the cartridge 10 nor will the tip of the probe 120 impact the bottom of the cartridge 110, clear advantages in the automated clinical chemistry analyzer art.

Conviniently, to remove the cartridge 10 from the carousel 98, the storage compartment 20 is grasped and the cartridge 10 is raised slightly, disengaging the portions 72 and teeth 74 from the notches 112, enabling the cartridge 10 to be easily radially removed from the slot 106 within the carousel 98.

Thus, the reagent cartridge of the present invention holds a plurality of reagents in compartments which do not share common walls, decreasing the likelihood of reagent migration and contamination and thus increasing shelf life and long-term reagent stability. The cartridge 10 of the present invention can be easily placed onto a reagent cartridge carousel yet is firmly retained by the carousel until the cartridge 10 is ready for removal. The collars 62 and teeth 74 provide a precise indexing means for the cartridge, allowing reagent probes to be inserted into the cartridge with no risk of collision between the probe tip and the top or bottom of the cartridge. Furthermore, the bottom member 14 of the cartridge 10 includes depressions 80, 82 and 84 which provide an additional margin of safety for the reagent probe and enable the reagent cartridge to deliver more usable reagent to the automated analyzer.

It is to be recognized that the scope the present invention is not to be limited to the particular embodiment disclosed herein but is to be defined only in accordance with the appended claims.

What is claimed is:

1. A reagent cartridge comprising:
   a plurality of storage compartments, the compartments collectively forming a wedge shaped arrangement, each compartment including a top wall and a bottom wall;
   at least one support member, the at least one support member being spaced a predetermined distance from the bottom wall of at least one of the storage compartments; and
   positioning means associated with the reagent cartridge for engaging suspension means whereby the reagent cartridge may be maintained in a suspended manner.

2. A reagent cartridge comprising:
   a plurality of separate storage compartments, the compartments collectively forming a wedge shaped arrangement, each compartment including a top wall and a bottom wall, at least one top wall defining a plane extending over the compartments;
   at least one support member above the plane, the at least one support member being spaced a predetermined distance from the bottom wall of at least one of the storage compartments, and the reagent cartridge being adapted for support by suspension means whereby the reagent cartridge may be held in a suspended manner; and
   positioning means associated with the reagent cartridge for engaging the suspension means whereby the reagent cartridge may be held in a predetermined position.

3. A reagent cartridge comprising:
   a plurality of integrally connected storage compartments, wedge shaped in arrangement, each compartment including a top and bottom wall, at least one support member spaced above the bottom wall for engaging suspension means whereby said at least one support member is adapted to suspend the reagent cartridge.

4. A reagent cartridge comprising:
   a plurality of independent storage compartments in fixed rigid relationship to each other, each including a top wall and a bottom wall, wall members for each compartment separate from each other, the top wall or bottom wall of one of the storage compartments defining a storage compartment width, the compartments being located adjacently in a line and having a decreasing width from one end of the line to the other;
   at least one suspending support member affixed relative to the top wall of at least one of the storage compartments, the suspending support member being spaced a predetermined distance from the bottom wall of at least one of the storage compartments; and
   a tooth projecting from at least one of the suspending support members.

5. A reagent cartridge as in claim 4 including a support member related to each compartment and wherein the support member includes an upstanding neck, the neck defining an access opening through the top wall.

6. A reagent cartridge as in claim 5 wherein the reagent cartridge further includes a top member formed integrally with each top wall, the top member holding the storage compartments in a fixed relationship and separating the respective storage compartment wall members.

7. A reagent cartridge as in claim 5 wherein the reagent cartridge further includes a bottom member formed integrally with each bottom wall, the bottom member holding the storage compartments in a fixed relationship and separating the separate storage compartment wall members.

8. A cartridge having a generally wedge shape width comprising:
   a plurality of storage compartments each including a top wall and a bottom wall, the top or bottom wall of one of the storage compartments defining a storage compartment width, the compartments being adjacently located in a line and having a decreasing width from one end of the line to the other whereby the width of adjacent compartments tapers relatively towards one end of the line, such that each compartment has a width commensurate with the wedge shape width;
   a support member above the top wall of at least one of the storage compartments, the support member being spaced a predetermined distance from the bottom wall of at least one of the storage compartments; and
   a tooth projecting from the support member.

9. A reagent cartridge as in claim 8 wherein the storage compartments each include wall members and the reagent cartridge further includes a top member formed integrally with each top wall, the top member holding the storage compartments in a fixed relationship and separating the respective compartment wall members.

10. A reagent cartridge as in claim 8 wherein the storage compartments each include wall members and the reagent cartridge further includes a bottom member formed integrally with each bottom wall, the bottom member holding the storage compartments in a fixed relationship and separating the respective storage compartment wall members.

11. A reagent cartridge comprising:
    at least one storage compartment, the compartment being generally a wedge shaped arrangement, the compartment including a top wall and a bottom wall;
    at least one support member, the support member being positioned and arranged relative to the top wall a predetermined distance from the bottom wall of the at least one storage compartment; and positioning means associated with the reagent cartridge for engaging suspension means whereby the reagent cartridge may be maintained in a suspended manner.

12. A reagent cartridge comprising:
a plurality of separate storage compartments, each compartment including a top wall and a bottom wall, at least one top wall defining a plane extending over the compartments, and the compartments being of different volumes relative to each other, and each compartment having upwardly directed wall means, the upwardly directed wall means of each compartment being separate from the upwardly directed wall means of other compartments;
an integral member formed with each compartment, the integral member holding the storage compartments in a fixed rigid relationship;
at least one suspending support member above the plane, the suspending support member being spaced a predetermined distance from the bottom wall of at least one of the storage compartments, and the reagent cartridge being adapted for support by suspension means whereby the reagent cartridge may be held in a suspended manner and the suspending support member being non-movably located relative to the reagent cartridge; and
positioning means associated with the reagent cartridge for engaging the suspension means whereby the reagent cartridge may be held in a predetermined position.

13. A reagent cartridge as in claim 12 including a support member related to each compartment and wherein the support member includes an upstanding neck, the neck defining an access opening through the top wall.

14. A reagent cartridge as claimed in claim 12 wherein the positioning means includes a tooth projecting from said at least one suspending support member.

15. A reagent cartridge for use in a clinical analyzer comprising an integral member constructed so as to define an arrangement of storage compartments in a fixed rigid relationship, the storage compartments each including a top and bottom wall and the compartments being of different volumes relative to each other and each compartment having upwardly directed wall means, the upwardly directed wall means of each of said compartments being separate from the upwardly directed wall means of the other of said compartments; and
at least one support member spaced above the bottom wall of one of said compartments and positioning means fixedly associated with the reagent cartridge for engaging suspension means whereby said reagent cartridge may be maintained in a suspended manner in a storage apparatus of a clinical analyzer.

16. A reagent cartridge for use in a clinical instrument, wherein the clinical instrument includes a reagent cartridge storage apparatus including means adapted to support the reagent cartridge, the reagent cartridge comprising:
a plurality of storage compartments, the compartments forming collectively a wedge shaped arrangement, each including a top wall and a bottom wall, the top wall of one of the storage compartments defining a storage compartment width;
one or more support member surfaces atop the top wall of at least one of the storage compartments, the support member surfaces defining a plane spaced a distance from a bottom wall of at least one of the storage compartments; and
means associated with the reagent cartridge for engaging suspension means whereby said reagent cartridge may be maintained in a suspended manner.

17. A reagent cartridge for use in a clinical instrument, wherein the clinical instrument includes a reagent cartridge storage apparatus including means adapted to support the reagent cartridge, the reagent cartridge comprising:
a plurality of storage compartments each compartment being in fixed rigid relationship relative to each other, the fixed relationship being defined by an integral member extending between all the compartments, and the compartments being of different volume and including a top wall and a bottom wall;
necks formed at the top walls of the storage compartments, the necks defining access openings through the top walls;
collars about the necks, the collars defining a plane spaced a distance from the bottom walls of the storage compartments; and
a tooth relative to the collars and projecting from the plane defined by the collars for movably retaining the reagent cartridge.

18. A reagent cartridge storage apparatus including a carousel for storing a reagent cartridge, the reagent cartridge having a generally wedge shape width for use in the carousel, wherein the carousel includes means adapted to support the reagent cartridge on the carousel, the reagent cartridge comprising:
a plurality of storage compartments each including a top wall and a bottom wall, the top or bottom wall of one of the storage compartments defining a storage compartment width, the compartments being adjacently located in a line and having a decreasing width from one end of the line to the other whereby the width of adjacent compartments taper relatively towards one end of the line, such that each compartment has a width commensurate with the wedge shape width;
a support member above the top wall of at least one of the storage compartments; the support member being spaced a predetermined distance from the bottom wall of at least one of the storage compartments; and
a tooth projecting from the support member.

19. A reagent cartridge storage apparatus including a carousel for storing a reagent cartridge for use in a clinical instrument, wherein the carousel includes means adapted to support the reagent cartridge on the carousel, the reagent cartridge comprising:
a plurality of spaced storage compartments, the compartments forming collectively a wedge shaped arrangement, each including a top wall and a bottom wall;
one or more support members, one or more of the support members defining a plane spaced a distance from the bottom wall of the storage compartments; and
a member defined by one or more support member surfaces for movably suspending the reagent cartridge.

20. A reagent cartridge storage apparatus comprising a reagent cartridge for use in a clinical instrument, wherein the clinical instrument includes carousel for storing the reagent cartridge and means adapted to support the reagent cartridge, the reagent cartridge comprising a plurality of integrally connected storage compartments, wedge shaped in arrangement, each storage compartment including a top and bottom wall, at least one suspending support member spaced above the bottom wall of one of the storage compartments, and tooth means associated with the suspending support member for engaging the support means on the carousel whereby said reagent cartridge may be maintained in a supported manner.

21. A reagent cartridge storage apparatus including a carousel for storing a reagent cartridge for use in a clinical instrument, wherein the carousel includes means adapted to support the reagent cartridge on the carousel, the reagent cartridge comprising:
   a plurality of storage compartments, the compartments collectively forming a wedge shaped arrangement, each compartment including a top wall and a bottom wall;
   at least one support member, the at least one support member being spaced a predetermined distance from the bottom wall of at least one of the storage compartments; and
   positioning means associated with the cartridge for engaging suspension means whereby the reagent cartridge may be maintained in a suspended manner.

22. A reagent cartridge storage apparatus including a carousel for storing a reagent cartridge for use in a clinical instrument, wherein the carousel includes means adapted to support the reagent cartridge on the carousel, the reagent cartridge comprising:
   a plurality of separate storage compartments, the compartments collectively forming a wedge shaped arrangement, each compartment including a top wall and a bottom wall, at least one top wall defining a plane extending over the compartments;
   at least one support member above the plane, the at least one support member being spaced a predetermined distance from the bottom wall of at least one of the storage compartments, and the reagent cartridge being adapted for support by the support means, said support means including suspension means whereby the reagent cartridge may be held in a suspended manner; and
   positioning means associated with the reagent cartridge for engaging the suspension means whereby the reagent cartridge may be held in a predetermined position.

23. A reagent cartridge storage apparatus including a carousel for storing a reagent cartridge for use in a clinical instrument, wherein the carousel includes means adapted to support the reagent cartridge on the carousel the reagent cartridge comprising:
   a plurality of integrally connected storage compartments, wedge shaped in arrangement, each compartment, including a top and bottom wall, at least one support member spaced above the bottom wall, said support means including suspension means whereby said at least one support member is adapted to suspend the reagent cartridge.

24. A reagent cartridge storage apparatus including a carousel for storing a reagent cartridge for use in a clinical instrument, wherein the carousel includes means adapted to support the reagent cartridge on the carousel, the reagent cartridge comprising:
   a plurality of integrally connected storage compartments, wedge shaped in arrangement, each compartment including a top and bottom wall, at least one support member spaced above the bottom wall and tooth means associated with the at least one support member for engaging the carousel, said at least one support member including suspension means whereby said reagent cartridge may be maintained in a suspended manner.

25. A reagent cartridge storage apparatus including a reagent cartridge having a generally wedge shape width for use in a clinical instrument, wherein the clinical instrument includes a carousel for storing the reagent cartridge and carousel means adapted to support the reagent cartridge, the reagent cartridge comprising:
   a plurality of storage compartments each including a top wall and a bottom wall, the top or bottom wall of one of the storage compartments defining a storage compartment width, the compartments being adjacently located in a line and having a decreasing width from one end of the line to the other whereby the width of adjacent compartments tapers relatively towards one end of the line, such that each compartment has a width commensurate with a the wedge shape width;
   a support member position of and arranged above the top wall of at least one of the storage compartments, the support member being spaced a predetermined distance from the bottom wall of at least one of the storage compartments; and
   a tooth projecting from the support member.

26. A reagent cartridge storage apparatus including a carousel for storing a reagent cartridge for use in a clinical instrument, wherein the carousel includes means adapted to support the reagent cartridge on the carousel, the reagent cartridge comprising:
   at least one storage compartment, the compartment being generally a wedge shaped arrangement, the compartment including a top wall and a bottom wall;
   at least one support member, the support member being spaced a predetermined distance from the bottom wall of the at least one storage compartment; and
   positioning means associated with the reagent cartridge for engaging the support means, said support means including suspension means whereby the cartridge may be maintained in a suspended manner.

27. A reagent cartridge storage apparatus as claimed in anyone of claims 18 to 26 including a reagent in at least one of the storage compartments of the cartridge.

* * * * *